US00RE38711E

(19) United States
(12) Reissued Patent
Igaki et al.

(10) Patent Number: US RE38,711 E
(45) Date of Reissued Patent: *Mar. 15, 2005

(54) LUMINAL STENT, HOLDING STRUCTURE THEREFOR AND DEVICE FOR ATTACHING LUMINAL STENT

(75) Inventors: Keiji Igaki, Kyoto (JP); Hideo Tamai, Moriyama (JP)

(73) Assignee: Kabushikikaisha Igaki Iryo Sekkei, Kyoto (JP)

( * ) Notice: This patent is subject to a terminal disclaimer.

(21) Appl. No.: 10/287,743

(22) Filed: Nov. 5, 2002

Related U.S. Patent Documents

Reissue of:
(64) Patent No.: 6,080,177
Issued: Jun. 27, 2000
Appl. No.: 09/069,003
Filed: Apr. 28, 1998

U.S. Applications:
(63) Continuation of application No. 08/794,396, filed on Feb. 5, 1997, now Pat. No. 6,045,568, which is a continuation of application No. 08/398,047, filed on Mar. 2, 1995, now abandoned, which is a continuation of application No. 07/946,297, filed as application No. PCT/JP91/01601 on Nov. 20, 1991, now abandoned.

(30) Foreign Application Priority Data

Mar. 8, 1991 (JP) ..... P3-068933
Oct. 7, 1991 (JP) ..... P3-324960

(51) Int. Cl.[7] ..... A61M 29/00

(52) U.S. Cl. ..... 606/198; 606/108; 606/194; 623/1.11; 623/1.2

(58) Field of Search ..... 606/108, 192, 606/198, 194, 195; 623/1.11, 1.2, 1.49, 1.5

(56) References Cited

U.S. PATENT DOCUMENTS 4,950,227 A * 8/1990 Savin et al. ..... 606/198
5,085,629 A * 2/1992 Goldberg et al. ..... 606/198
5,147,399 A * 9/1992 Dellon et al. ..... 623/12
5,195,984 A * 3/1993 Schatz ..... 623/1.2
5,274,074 A * 12/1993 Tang et al. ..... 623/15

* cited by examiner

*Primary Examiner*—Kevin T. Truong
(74) *Attorney, Agent, or Firm*—Rader, Fishman & Grauer PLLC

(57) ABSTRACT

A luminal stent is a tubular body formed by knitting a sole yarn of a bioresorbable polymer fiber, such as fiber of polylactic acid, polyglycol acid or a polylactic acid—polyglycol acid copolymer. When introduced into and attached to the inside of the vessel by a catheter fitted with a balloon, the tubular member may retain its shape for several weeks to several months after attachment and subsequently disappears by being absorbed into the living tissue. In this manner, the luminal stent is not left as a foreign matter semi-permanently in the living body without producing inflammation or hypertrophy in the vessel. There is also provided a method for attaching the luminal stent in the vessel.

13 Claims, 7 Drawing Sheets

LUMINAL STENT, HOLDING STRUCTURE THEREFOR AND DEVICE FOR ATTACHING LUMINAL STENT

Matter enclosed in heavy brackets [ ] appears in the original patent but forms no part of this reissue specification; matter printed in italics indicates the additions made by reissue.

This application is a continuation of Application Ser. No. 08/794,396 filed Feb. 5, 1997, *now U.S. Pat. No. 4,045,568* which is in turn a continuation Application Ser. No. 08/398,047 filed Mar. 2, 1995, abandoned, which is in turn a continuation of abandoned, Application Ser. No. 07/946,297 filed Nov. 2, 1992, which was the National Stage of International Application No. PCT/JP91/01601 filed Nov. 20, 1991.

TECHNICAL FIELD

This invention relates to a stent introduced into a vessel, such as a blood vessel, lymph vessel, bile duct or ureter for maintaining the shape of the vessel. More particularly, it relates to a luminal stent attached to a site of angioplasty after the operation of percutaneous angioplasty of a stenotic part of the blood vessel, such as artery (the operation of introducing a balloon forming portion annexed to the end of a catheter into a constricted portion of the blood vessel for forming a ballooning for dilating the constricted portion for improving blood flow) and a device for attaching the luminal stent.

BACKGROUND TECHNOLOGY

As this type of the luminal stent, there is known a tubular stent constituted by wrapping a meshed structure formed by intertwining longitudinal and transverse wires of e.g. stainless steel. Such tubular stent is introduced into the site of angioplasty and dilated there so as to be attached thereto.

This known type of the stent however suffers from the problems that it is hard and tends to stress the vessel to produce inflammation of hypertrophy in the vessel which may cause reconstriction in the vessel, and that the stent is semipermanently left as a foreign matter within the living body, which is inherently not desirable to the living body.

If the metal stent, which is left in the vessel semipermanently or for a time longer than is necessary, is attached within the vessel, it may occur that the stent turns out to be a kind of a nucleus and the risk is high that stenosis be again caused in the site of attachment of the stent. Besides, an injury done to the vessel around the stent tends to cause abnormal multiplication of living cells on the inner wall of the vessel to contract the vessel.

It is therefore an object of the present invention to provide a luminal stent free from the problems and a device for attachment of the stent.

DISCLOSURE OF THE INVENTION

According to the present invention, the above object is accomplished by a luminal stent consisting of a tubular member produced by knitting a bioresorbable polymer yarn, and a luminal stent attachment device comprising the luminal stent which is fitted over a balloon forming portion in the vicinity of a distal end of a catheter.

The bioresorbable polymers may be enumerated by polylactic acid(PLA), polyglycolic acid(PGA), polyglactin (PGA-PLA copolymer), polydioxanone, polyglyconate (copolymer of trimethylene carbonate and glycolide) and a copolymer of polyglycol acid or polylactic acid with ϵ-caprolactone.

The bioresorbable polymer may be admixed with a variety of materials, including pharmaceuticals. The materials may also be deposited on the fiber surface.

The luminal stent of the present invention is introduced into and attached to the site of angioplasty by a catheter fitted with a balloon and attached in place by dilating the balloon. The luminal stent may retain its shape for several weeks to several months after attachment and disappears in several months after attachment by being absorbed in the living tissue after lapse of several months after attachment.

If an X-ray impermeable agent is admixed in the bioresorbable polymer, the state of the luinal stent may be observed after attachment by irradiation of X-rays from outside.

BRIEF DESCRIPTION OF THE DRAWINGS

The present invention will be explained in detail by referring to the accompanying drawings in which:

FIG. 4A shows the attachment device in its entirety and FIG. 4B shows a part thereof in cross-section.

FIG. 7A shows the illustrative vessel, FIG. 7B shows the state of attachment of the luminal stent of the present invention, and FIG. 7C shows an undesirable state of attachment of a conventional luminal stent, for comparison sake.

BEST MODE FOR CARRYING OUT THE INVENTION

Basically, the luminal stent of the present invention is fabricated by knitting a sole yarn, so that a tubular product as a luminal stent which is more homogenous than a fabric formed by weaving a so-called warp yarn and a weft yarn may be produced.

Besides, it is far easier for the knitted luminal stent of the present invention to pass through various meandering vessels before reaching the target site. That is, the luminal stent formed from a knitted cloth exhibits trackability with respect to a variety of meandering passages, while it can be introduced into and attached to a site of bend, because the tubular knitted product tends to be a dilated and is not likely to mar the shape of the lumen. According to the present invention, the tubular wove stent having a diameter of about 5 mm is heat-treated and set so as to be contracted in diameter to about 2 mm or less for being introduced into and attached to the inside of the vessel of a lesser diameter in the living body than the stent. This process is explained by referring to FIG. 1.

Figure 2:
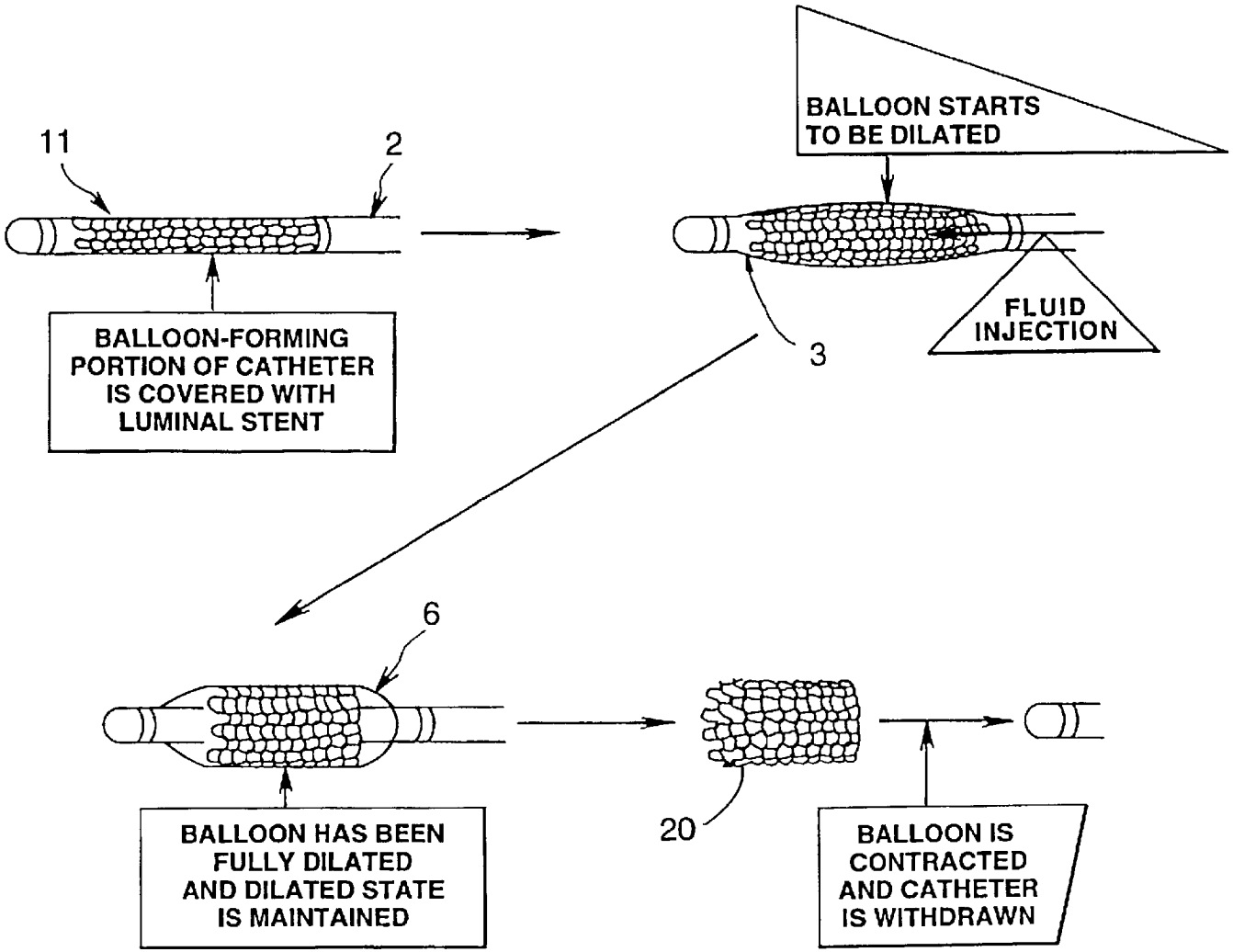
FIG. 2 is a conceptual view showing the luminal stent of the present invention as it is introduced into and attached to the vessel.

The process of attachment of the heat-set luminal stent to the inside of the vessel is shown in a conceptual view of FIG. 2.

Figure 3:
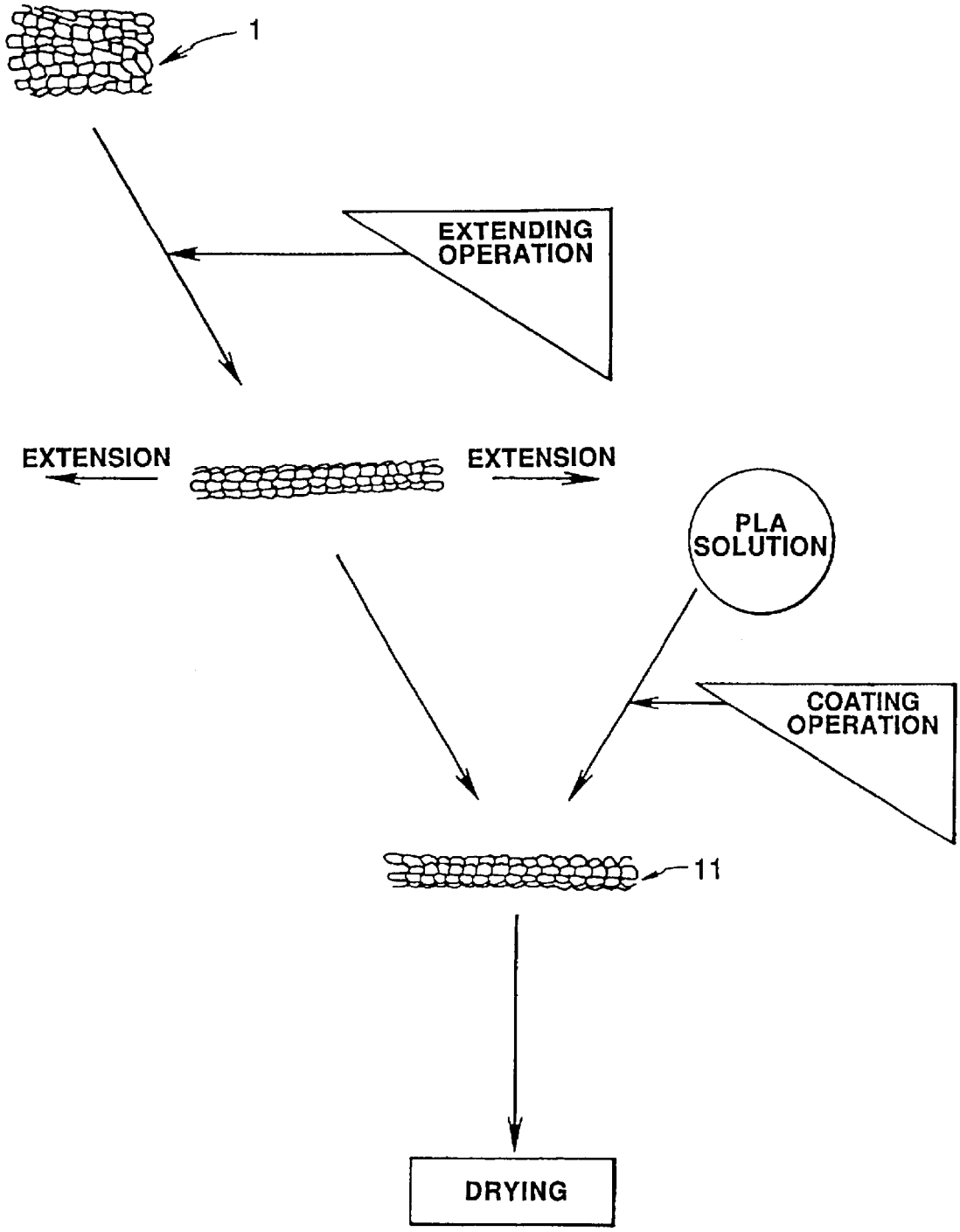
FIG. 3 shows an alternative method for contracting the luminal stent, woven from a yarn of PGA fibers of the present invention, in the direction along its diameter.

An alternative method of contracting the luminal stent 1 knitted from PGA (polyglycolic acid) polymer fiber is shown in FIG. 3. The method shown in FIG. 3 has an advantage that, since a tube formed of metal or a heat-resistant resin is not used, the stent can be directly attached to a ballooning portion at the distal end of the catheter.

The present invention provides a tubular luminal stent formed by knitting a sole yarn of a biologically resorbable polymer fiber. The luminal stent is superior in pliability and shape retention properties to other cloth forms, such as a non-woven fabric, e.g. a felt, or a woven fabric formed by weaving weft and warp yarns. The knitted luminal stent is additionally heat set for exhibiting more prominent effects in pliability and shape retention characteristics.

Figure 1:
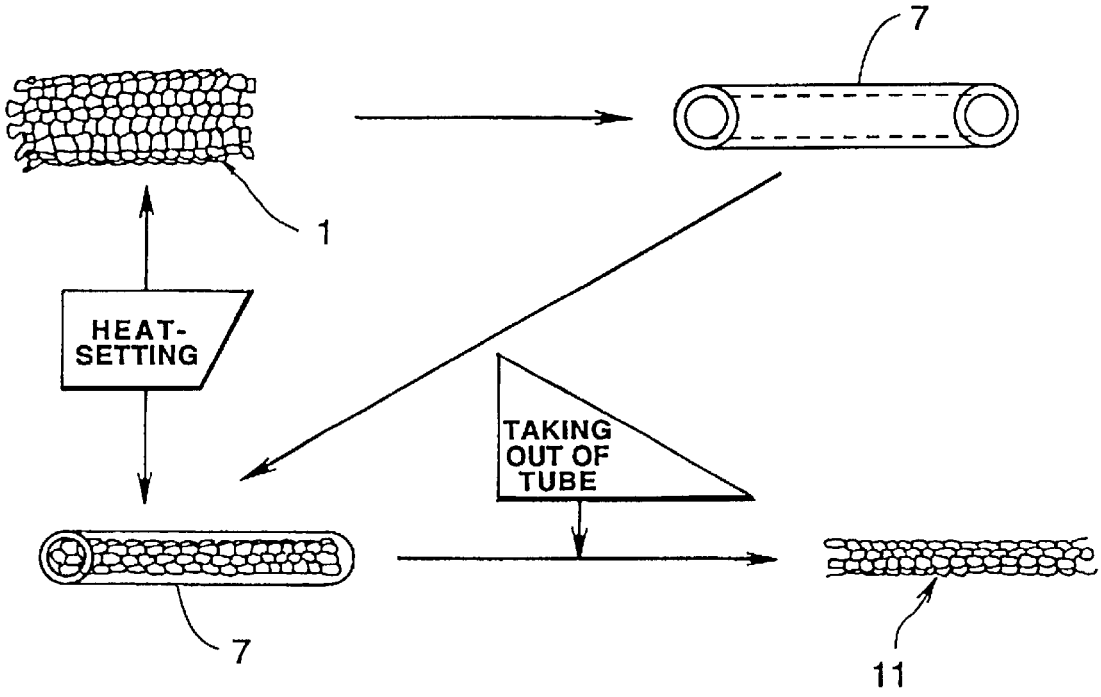
FIG. 1 shows the process of producing a luminal stent according to the present invention, in the diametrically contracted state.

The tubular luminal stent 1 knitted from a yarn of a bioresorbable polymer fiber, has a diameter of an order of 4 to 5 mm and is heat set after it is introduced or as it is introduced into a tube 7 of heat-resistant resin or metal having an inside diameter of about 1 to 3 mm, preferably 2 mm, to produce a luminal stent 11 having a set shape with a diameter of about 2 mm, as shown in FIG. 1.

Besides, the heat setting has such a meaning that, by heat-treating (heat-setting) the knitted tubular luminal stent while it has a large diameter, or after it is contracted in diameter, the knitted fabric has terminal fibers, yarns or meshes which are excellent in shape retention characteristics, such that the heat setting affords superior shape retention characteristics while minimizing the stress otherwise applied to the inner wall of the vessel of the living body.

By using the PLA+PGA as bioresorbable polymer fibers, and by changing the mixing ratio, the half value period in strength of the luminal stent of the present invention, that is the period in which the bioresorbability disappears, may be freely combined within a time period of from three weeks to three months.

Besides, by adding an X-ray impermeable agent at the time of spinning the fibers, the state of the introduced luminal stent may be observed with X-rays. Thrombus lysing agents or anti-thrombotic agents, such as heparin, urokinase or t-PA may also be added, if so desired.

Besides, by taking advantage of the fact that the luminal stent of the present invention, produced by knitting a yarn of the bioresorbable polymer fibers, is vanished after a predetermined time lapse from the site into which it has been introduced, carcinostatics of anti-thrombotic agents may be mixed into or attached to the fibers of concentrated administration of these agents to the site of lesion.

In addition, the fibers used in knitting the luminal stent of the present invention may be rendered variable in the cross-sectional shape thereof more easily than if the luminal stent is formed from metal. That is, affinity with the living body or shape retention characteristic may be controlled by affording the hollow or profiled cross-sectional shape to the filaments during spinning or by using a monofilament yarn or a multifilament yarn.

Besides, the yarn of synthetic polymers may be processed in many ways on its fiber surface. That is, using a yarn having a substantially circular cross-section as usual and which is not processed in any particular manner on its surface, a yarn having the above-mentioned so-called profiled cross-section, or the above-mentioned processed yarn, anti-thrombotic materials, thrombus-lysing agents or cells of the living bodies may be attached to this yarn for promoting multiplication of the endothelial cells. Alternatively, X-ray non-transmitting materials may also be attached to the yarn.

Meanwhile, if it is desired to dilate the stenotic site of the vessel to the diameter of, for example, 4 mm, and to maintain the diameter, the site is not dilated at a time. That is, for avoiding an abrupt stress to the vessel or to the living body per se, the vessel is first dilated to a diameter of 3 mm by an extender having a balloon-forming portion of a diameter of 0.8 to 1.2 mm. After the catheter 2 fitted with a ballooning portion 3 is extracted, a catheter not fitted with a luminal stent and fitted only with the balloon-forming portion 3 is introduced into the vessel for dilating the vessel to a diameter of 4 mm or more. Finally, the knitted luminal stent 11 is attached in place by a luminal stent attachment device in which a luminal stent 11 according to the present invention is attached to the balloon forming portion 3 of the device. However, it is not absolutely necessary to dilate the vessel by steps in this manner, and the luminal stent 11 may be introduced into and attached to the target site after the stenotic portion of the vessel is dilated at a time to the desired diameter.

Alternatively, a luminal stent attachment device per se, which is the catheter fitted with the ballooning device and with the luminal stent of the present invention, may be used for introducing and attaching the luminal stent into the vessel of the living body simultaneously with vessel dilation.

Figure 4:
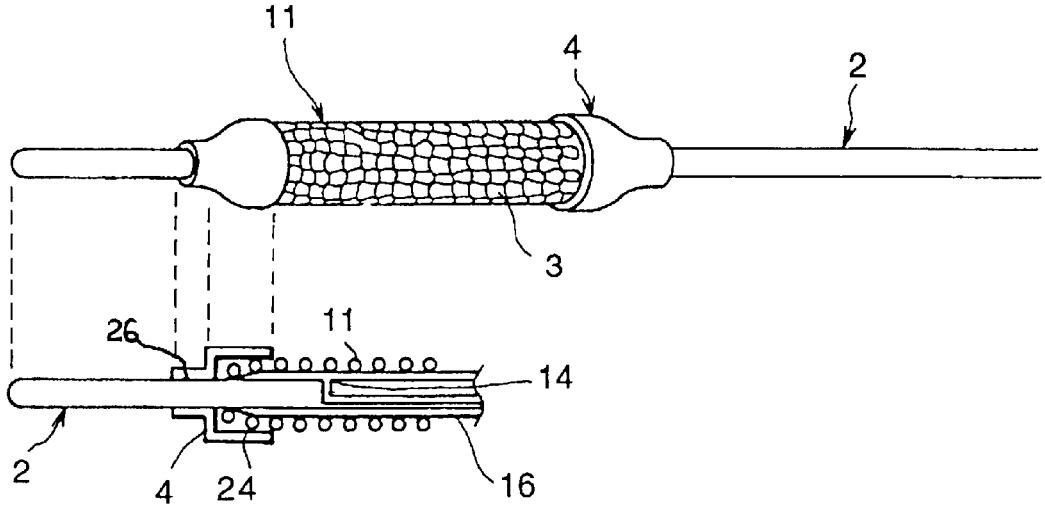
FIGS. 4A and 4B are schematic views showing essential parts of a device for attachment of the luminal stent according to the present invention, where

The device for introducing and attaching the luminal stent of the present invention in the stenotic portion of the vessel of the living body is explained in detail. In the vicinity of the distal end of the catheter 2, there exists a region capable of forming a balloon 6 of a desired diameter by a gas or a liquid, such as an X-ray contrast medium, which is injected via a hollow part within the catheter 2 under a liquid pressure of 8 to 10 atmospheres. The above-mentioned heat-set luminal stent, having the diameter of about 2 mm, is applied over the balloon forming portion 3, which is about 20 mm long, with both ends of the luminal stent 11 being clamped by holding members 4 of silicone resin or the like between the catheter 2 (at fitting part 26) and the outer periphery of the balloon-forming forming thin film 16 (at holder 24), as shown in FIG. 4.

However, the length of the balloon forming portion 3 or the diameter of the luminal stent 11 may be optionally set depending on the types of the luminal stent or the specific nature of the vessel.

Meanwhile, the distal end of the catheter is occasionally provided with a guide wire which plays the role of a guide wire when the catheter is introduced into the vessel.

For attachment of the luminal stent, a communication orifice 14 (see FIG. 4B) is formed at a mid part along the length of the balloon forming portion 3 of the catheter 2 for permitting the fluid injected for forming the balloon to exit from the hollow part of the catheter to be charged between the hollow part of the catheter and the balloon-forming thin film 16. A balloon is formed by being dilated under a fluid pressure of 8 to 10 atmospheres via the orifice and maintained for 30 to 60 seconds or for a longer time. The stent 11 undergoes a kind of plastic deformation at this time under the force of dilation of the balloon so as to be maintained in the dilated state 20. At this time, the polymer itself is changed in the molecular level, or the knitted structure, that is the mesh shape, is changed, that is, the stent 11 is contracted along its length and dilated along its radius so as to be changed in shape to maintain the thus changed shape.

Figure 5:
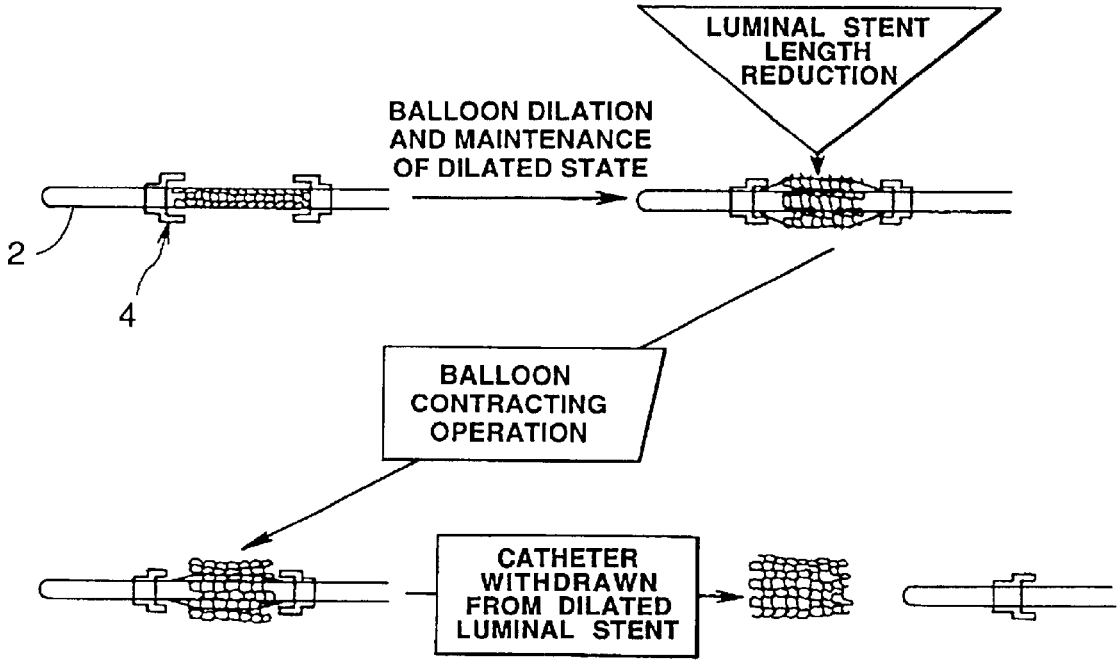
FIG. 5 is an explanatory view showing the process of attachment of the luminal stent by the attachment device of the present invention.

FIG. 5 shows the process of introducing and attaching the luminal stent of the present invention within the vessel of a living body. As shown therein, the luminal stent is contracted in length with balloon dilation so that both ends of the stent are detached from the holding members 4. By the subsequent operation of contracting the balloon, the catheter 2 may be removed in its entirety.

Figure 6:
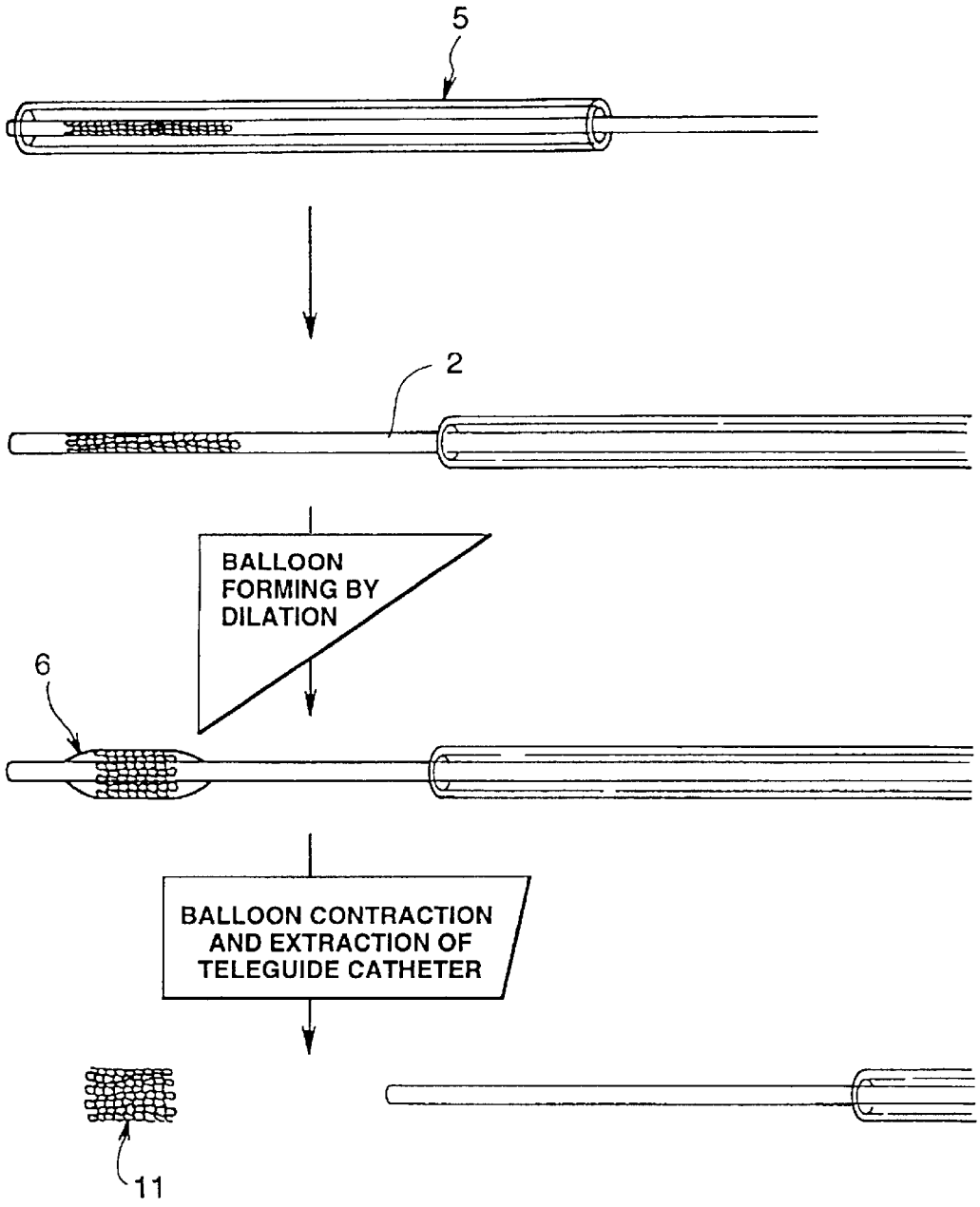
FIG. 6 shows another embodiment of the attachment device of the luminal stent according to the present invention.

FIG. 6 shows another example of a luminal stent attachment device according to the present invention. In this case, the catheter 2 fitted with a balloon 6 is covered with a sheath 5 a teleguide catheter and introduced in this state into the vessel of the living body. Then, with the sheath 5 extracted slightly, the balloon 6 is dilated and maintained in the dilated state. The balloon 6 is then contracted and the sheath 5 is extracted simultaneously with the catheter 2, while the luminal stent 11 is left in the vessel.

Meanwhile, the thin film for balloon forming may be formed of a variety of synthetic polymeric materials, such as polyethylene terephthalate or polyethylene.

Figure 7A:
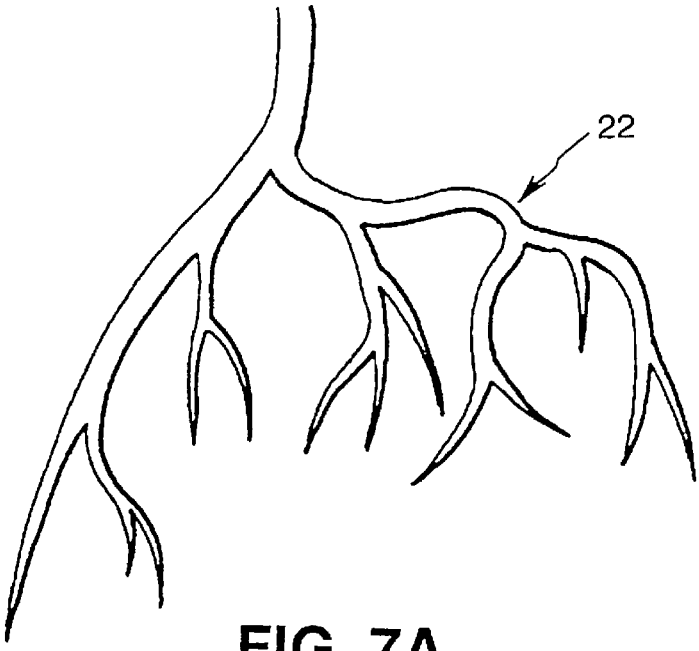
FIGS. 7A, 7B and 7C show the state of attachment between the vessel and the luminal stent, where
Figure 7B:
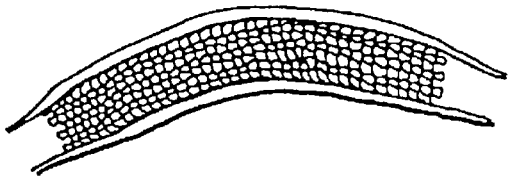
Figure 7C:
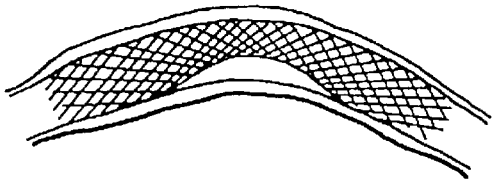

It is noted that the luminal stent of the present invention may be introduced into a bend in the vessel so as to adapt itself to the bent shape of the vessel, as best shown in FIG. 7B. On the other hand, FIG. 7C shows the state in which a metal stent consisting in a tubular mesh or screen formed by weaving a weft material and a warp material or a stent of a woven fabric is introduced into a bend in the vessel. The metal stent or the stent of the woven fabric is bent at a bend of the vessel so that the shape of the vessel cannot be correctly maintained in the site of the bend. Meanwhile, the luminal stent of the present invention is superior in follow-up characteristics so that it can reach the target site even if there exist branched parts in the vessel, as discussed previously. FIG. 7A shows an example of the vessel of the living body in which it is assumed that a site 22 shown by an arrow therein be the target site for attachment of the luminal stent.

Figure 8:
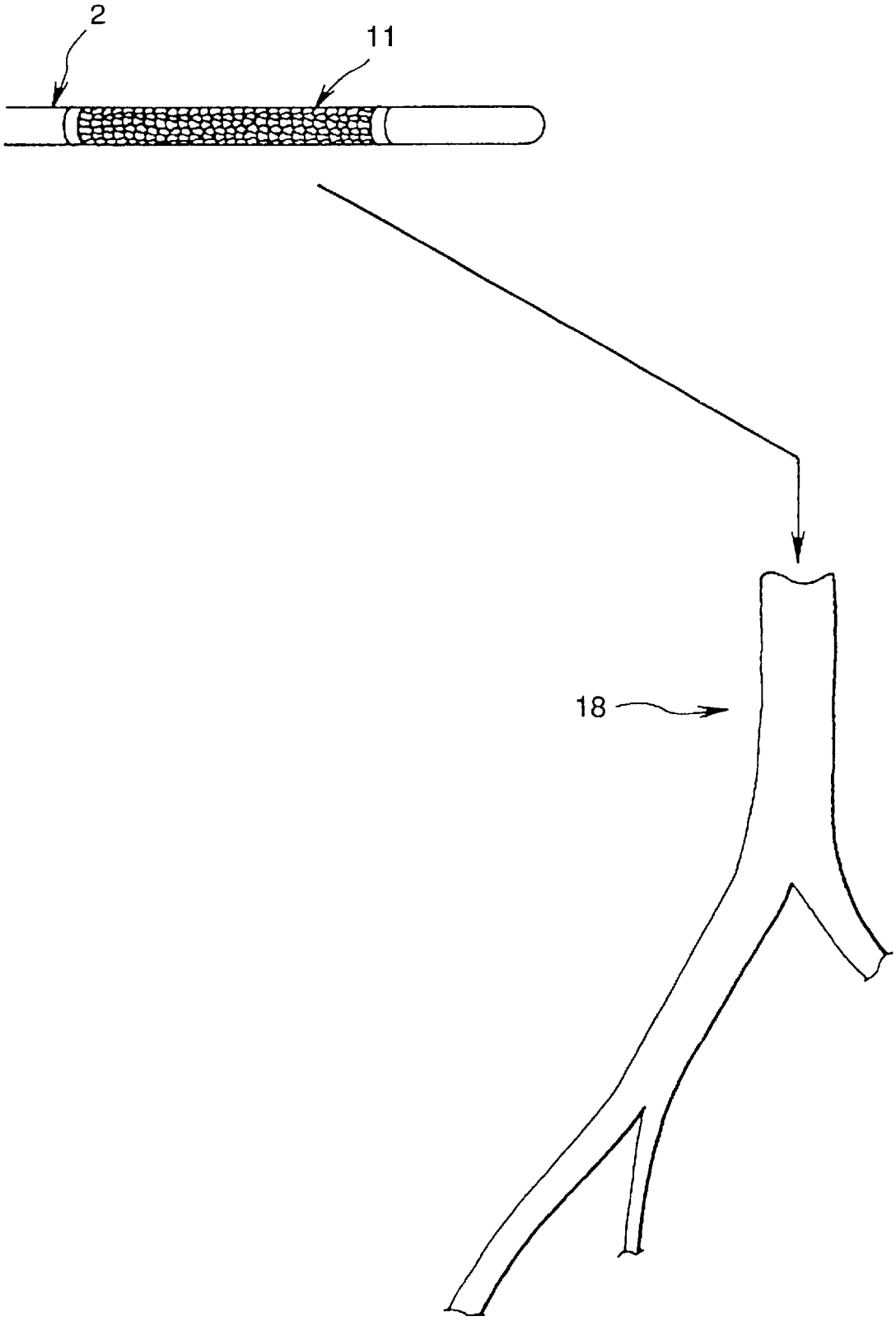
FIG. 8 shows the possibility of attachment of the luminal stent of the present invention in various vessel sites.

The luminal stent knitted from a yarn of the bioresorbable polymer fiber and heat-set according to the present invention may cope with any thickness of the vessel with the use of the luminal stent attachment device of the present invention. If, for example, the luminal stent is loaded in an attachment device which is dilated to a diameter of about 4 mm on dilating the balloon, the luminal stent may be attached to the vessel site having a diameter of 2.4 mm by controlling the degree of dilation of the balloon. The luminal stent may similarly be attached to the vessel site having a diameter of 3 or 4 mm. That is, the luminal stent 11 may be introduced and attached in any site of a luminal 18 shown in FIG. 8 by using the same catheter 2 fitted with the balloon. It is because the inside diameter of the luminal stent may be maintained of the thickness of the dilated balloon.

If re-constriction of the vessel should occur in several months after the luminal stent of the present invention is decomposed and absorbed into a living body, the luminal stent may again be introduced and attached in the same site. This is rendered possible by using the bioresorbable polymer.

Meanwhile, if a thin sheet of a non-woven fabric of a bioresorable polymer, such as a felt, bent into a shape of a tube, exhibits shape retention characteristics and flexibility comparable to those of the luminal stent of the present invention, such sheet may be used in place of the knitted material.

With the above-described luminal stent of the present invention, such meritorious effects may be achieved that inflammation or excess hypertrophy of the vessel may be prevented and consequently reconstriction of the vessel may be inhibited. The luminal stent of the present invention is absorbed in several months into a living tissue, which is favorable for the living body.

If an X-ray impermeable agent is applied to the bioresorbable polymer fibers or yarns of the luminal stent of the present invention, the state of attachment of the stent within the vessel may be easily observed by X-ray irradiation from outside.

Besides, the luminal stent may be applied over the balloon forming portion of the catheter according to the present invention so that the stent may be easily attached in the desired site within the vessel.

[Experiment 1

Plural luminal stents formed by knitting a yarn of polylactic acid fibers admixed with barium sulfate were introduced and attached in the coronary of a test animal in a tubular state of 4 mm in diameter and 20 mm in length by using a catheter fitted with a balloon, and the state of attachment was observed by irradiation of X-rays. It was seen that the stents substantially maintained their shape until after about three to six months. It was seen that the stents disappeared by being absorbed into living tissue in about 6 to 12 months. During this time, no abnormalities such as inflammation or hypertrophy of the intima of the blood vessel were observed.]

[Experiment 2

Plural luminal stents formed by knitting a yarn of polyglycolic acid fibers admixed with barium sulfate were introduced and attached in the femoral artery of a test animal in a tubular state of 4 mm in diameter and 20 mm din length and the state of attachment was observed by irradiation of X-rays. It was seen that the stents substantially maintained their shape until after about two to three weeks and were absorbed into the living tissue in about two to three months. The shape retention period and the period of existence in the living body attained in Experiment 2 are thought to be more safe than the corresponding periods attained in Experiment 1. Meanwhile, no inflammation or hypertrophy of the intima of the blood vessel was observed during these periods.]

What is claimed is:

1. A luminal stent, which is to be inserted into a vessel of a living body, consisting of a homogeneous tubular member produced by knitting a sole bioresorbable polymer fiber.

2. The luminal stent as defined in claim 1 wherein the bioresorbable polymer is polylactic acid (PLA).

3. The luminal stent as defined in claim 1 wherein the bioresorbable polymer is polyglycolic acid (PGA).

4. The luminal stent as defined in claim 1 wherein the bioresorable polymer is a mixture of polylactic acid (PLA) and polyglycolic acid (PGA).

5. The luminal stent as defined in claim 1 wherein the bioresorbable polymer is one or more of polyglactin (PGA-PLA copolymer), polydioxanone, polyglyconate (copolymer of trimethylene carbonate and glycolide) and copolymer of polyglycolic acid or polylactic acid with epsilon-caprolactone.

6. The luminal stent as defined in claim 1 wherein the cross-sectional shape of the sole bioresorbable polymer fiber is substantially circular, hollow or profiled.

7. The luminal stent as defined in claim 1 wherein the sole surface of the bioresorbable polymer fiber has irregularities or grooves.

8. The luminal stent as defined in claim 1 wherein the sole bioresorbable polymer fiber is admixed with one or more of X-ray impermeable agent, carcinostatics and anti-thrombotic agent.

9. The luminal stent as defined in claim 1 wherein the one or more of X-ray impermeable agents, carcinostatics and anti-thrombotic agents or cells of a living body are affixed to the surface of the sole bioresorbable polymer fiber.

10. The luminal stent as defined in claim 1 wherein a tubular body formed by knitting a sole bioresorbable polymer fiber is heat-set.

11. The luminal stent holding structure comprising the luminal stent as defined in claim 1 accommodated in a tube of a smaller inside diameter.

12. A luminal stent, which is to be inserted into a vessel of a living body, consisting of a homogeneous heat-set tubular member produced by knitting a sole bioresorbable polymer fiber.

13. A luminal stent, which is to be inserted into a vessel of a living body, consisting of a homogeneous double heat-set tubular member produced by knitting a sole bioresorbable polymer fiber.

* * * * *